United States Patent
Swoboda

(10) Patent No.: US 10,463,264 B2
(45) Date of Patent: Nov. 5, 2019

(54) PRESSURE/FORCE SENSORS HAVING A FLEXIBLE MEMBRANE, DYNAMIC AND STATIC PRESSURE/FORCE SENSOR CALIBRATION METHODS

(71) Applicant: Aqueduct Critical Care, Inc., Bothell, WA (US)

(72) Inventor: Marek Swoboda, Philadelphia, PA (US)

(73) Assignee: Aqueduct Critical Care, Inc., Bothell, WA (US)

(*) Notice: Subject to any disclaimer, the term of this patent is extended or adjusted under 35 U.S.C. 154(b) by 529 days.

(21) Appl. No.: 15/029,592

(22) PCT Filed: Oct. 14, 2014

(86) PCT No.: PCT/US2014/060401
§ 371 (c)(1),
(2) Date: Apr. 14, 2016

(87) PCT Pub. No.: WO2015/057648
PCT Pub. Date: Apr. 23, 2015

(65) Prior Publication Data
US 2016/0270678 A1    Sep. 22, 2016

Related U.S. Application Data

(60) Provisional application No. 61/961,403, filed on Oct. 15, 2013.

(51) Int. Cl.
*A61B 5/00* (2006.01)
*A61B 5/03* (2006.01)

(52) U.S. Cl.
CPC ............ *A61B 5/031* (2013.01); *A61B 5/0017* (2013.01); *A61B 5/0031* (2013.01);
(Continued)

(58) Field of Classification Search
CPC ......... A61B 5/03; A61B 5/031; A61B 5/0017; A61B 2562/0247; G01L 25/00; G01L 27/005
See application file for complete search history.

(56) References Cited

U.S. PATENT DOCUMENTS 4,206,762 A    6/1980  Cosman
4,658,829 A    4/1987  Wallace
(Continued)

FOREIGN PATENT DOCUMENTS

CN    1565662 A    1/2005
DE    41 30 601 A1    4/1992
(Continued)

*Primary Examiner* — Max F Hindenburg
(74) *Attorney, Agent, or Firm* — DWC Law Firm, P.S.; Ann W. Speckman

(57) ABSTRACT

An implantable pressure sensor that wirelessly provides pressure data to a wireless receiver. The pressure sensor includes a first flexible membrane exposed to the region whose pressure is being monitored. In contact with this first flexible membrane is a force transducer, for measuring this pressure, that is itself suspended on an internal flexible membrane. This internal flexible membrane allows the force transducer to not only be displaced away from the first flexible membrane, but it allows for the force transducer to also be oscillated, either out-of-contact with the first flexible membrane or in-contact therewith for static/dynamic pressure sensor calibration. Another embodiment suspends an internal housing on a third flexible membrane wherein the internal flexible membrane forms the upper surface of the internal housing. An actuator for displacing/oscillating the force transducer is located within the internal housing. This permits establishing a constant distance between the force transducer and the actuator.

11 Claims, 15 Drawing Sheets

(52) U.S. Cl.
CPC .... *A61B 5/6861* (2013.01); *A61B 2560/0238* (2013.01); *A61B 2562/0247* (2013.01)

(56) References Cited

U.S. PATENT DOCUMENTS

| | | |
|---|---|---|
| 5,291,899 A | 3/1994 | Watanabe et al. |
| 5,573,007 A | 11/1996 | Bobo, Sr. |
| 6,336,924 B1 | 1/2002 | Lecuyer et al. |
| 8,109,899 B2 | 2/2012 | Sundstrom et al. |
| 8,608,716 B2 | 12/2013 | Holper et al. |
| 2004/0260229 A1 | 12/2004 | Meir |
| 2005/0020962 A1 | 1/2005 | Reich et al. |
| 2006/0052737 A1 | 3/2006 | Bertrand et al. |
| 2007/0000333 A1 | 1/2007 | Brugger et al. |
| 2008/0052737 A1 | 2/2008 | Hamaguchi |
| 2009/0036754 A1 | 2/2009 | Pons et al. |
| 2010/0317977 A1 | 12/2010 | Piaget et al. |
| 2012/0302938 A1 | 11/2012 | Browd et al. |
| 2013/0197422 A1 | 8/2013 | Browd et al. |
| 2013/0247644 A1 | 9/2013 | Swoboda et al. |
| 2015/0112289 A1 | 4/2015 | Stebbins et al. |
| 2015/0196742 A1 | 7/2015 | Browd et al. |
| 2016/0067464 A1 | 3/2016 | Kim et al. |
| 2016/0101270 A1 | 4/2016 | Browd et al. |

FOREIGN PATENT DOCUMENTS

| | | |
|---|---|---|
| WO | 2011081669 A1 | 7/2011 |
| WO | 2011116393 A1 | 9/2011 |
| WO | 2012078861 A3 | 6/2012 |
| WO | 2012166980 A2 | 12/2012 |
| WO | 2015057648 A1 | 4/2015 |
| WO | 2015109260 A1 | 7/2015 |
| WO | 2015157320 A1 | 10/2015 |

PRESSURE/FORCE SENSORS HAVING A FLEXIBLE MEMBRANE, DYNAMIC AND STATIC PRESSURE/FORCE SENSOR CALIBRATION METHODS

CROSS-REFERENCE TO RELATED APPLICATIONS

This application is the US national phase entry of International Patent Application no. PCT/US2014/060401, filed Oct. 14, 2014, which claims benefit under 35 U.S.C. § 119(e) of Provisional Application Ser. No. 61/961,403 filed on Oct. 15, 2013 entitled INTERNAL DYNAMIC AND STATIC PRESSURE/FORCE SENSOR CALIBRATION. The entire disclosures of these applications are incorporated by reference herein.

This invention, or at least a portion of this invention, was made with government support under Grant Number: NS077523 awarded by the National Institutes of Health. The government has certain rights in the invention(s) developed with government support.

BACKGROUND OF THE INVENTION

1. Field of Invention

This present invention generally relates to medical devices and more particularly to implantable devices for monitoring internal pressure, e.g., intracranial pressure, of a living being.

2. Description of Related Art

Implantable sensors are important diagnostic devices which help measure physiological parameters that are difficult or even impossible to measure noninvasively. However, implantable devices pose several problems for the designer. They have to be biocompatible, so they do not harm the patient over a long or short term, and they cannot trigger physiological or patho-physiological reactions (e.g., immunological reactions) which can compromise their ability to perform measurements.

Another set of problems stems from engineering requirements. The stability requirements for the implantable sensor are more strict that those for the noninvasive devices since they cannot be calibrated at will, or at least, the calibration process is usually more challenging compared to other devices.

The long term implantable pressure sensors carry two inherent problems affecting their stability.

First, short term body temperature fluctuations change the internal temperature, thus changing the internal pressure. This pressure change affects the pressure differential between the internal pressure of the device and the external one (e.g., intracranial pressure, ICP). Another short term factor may include the change in the amount of gas inside the sensor body (e.g., gas absorption due to oxidation or gas release from materials inside the capsule). These types of changes can also add or subtract from forces acting on the transducer by changing forces acting on the membrane separating the inside of the sensor from the external environment. Another source of drift might be related to sensor aging. However, the use of solid state components assures the longevity of the materials.

Second, the natural body responses cause protein deposits on the outside surface of the device, thereby changing the effective stiffness of the membrane. This change in effective stiffness may change the sensitivity of the device or even entirely block the external pressure. This type of problem is usually associated with long term changes.

A typical solution to these problems is to utilize two identical sensors which respond to temperature and aging the same way. One sensor is usually exposed to the measured quantity while the reference one is only exposed to conditions inside the sensor housing. The resulting signal is calculated as a difference between the reference signal and the second sensor. However, this solution has several drawbacks: e.g., the reference pressure in the reference transducer has to be kept constant.

The above-listed problems (assuming that the membrane by itself does not generate any stress on the sensor regardless of the displacement, i.e., an ideal membrane) causes the output-input characteristic of the sensor to shift up or down (see FIG. 1A); or to rotate about certain point changing the slope of the characteristic (FIG. 1B). In particular, plot 1 of FIG. 1A depicts the undisturbed input-output characteristic. Plot 2 depicts the input-output characteristic of the internal pressure (i.e., inside the sensor body) which is lowered. Plot 3 depicts the input-output characteristic if the internal pressure is elevated.

Every sensor carries an inherent risk of drifting with time. While several compensation methods exist for external sensors, the drift problem is accentuated in the case of an implantable sensor. The active element of the sensor (e.g., piezoresistive element or die) changes its properties with time, temperature etc. FIG. 2 depicts the variance of output vs. measured quantity (e.g., pressure) as temperature changes. The lower line 2A in FIG. 2 represents the normal operation curve of the die when operating at a temperature $T_1$. The slope of this line 2A represents the sensitivity of the sensor at that temperature. If the temperature is increased, the piezoresistive die's response to changes in pressure also changes (see upper line 2B in FIG. 2); in particular, the sensitivity changes and also an offset component is introduced. Such factors can be resolved by hardware and, typically, sensor housings are constructed with built-in compensation. However, such solutions increase the size of the sensor and the power consumption.

One of the physiological parameters which is difficult to measure noninvasively is ICP. ICP can be an important parameter in monitoring hydrocephalic patients, or traumatic brain injury (TBI) victims.

Since cerebrospinal fluid is enclosed in a semi closed system (i.e., the skull), the forces exerted by it are counterbalanced by a rigid structure of bones and, to some extent, by a semi rigid structure of the spinal channel. In a mechanical sense, there is no direct link (except for some small vessels which are difficult to utilize due to their anatomical nature) between the cerebrospinal fluid and the external environment. Thus, an implantable sensor outfitted with a reliable means of calibration would be a valuable addition to neurosurgical armamentarium.

U.S. Patent Publication No. 2013/0247644 (Swoboda, et al.), which is owned by the same Assignee as the present application, namely, ICPCheck, Inc. of Bensalem, Pa., discloses a calibration system and method for an implantable pressure sensor having wireless communication capability. The inventions disclosed therein are directed to static calibration systems and methods of the implantable pressure sensor.

However, there remains a need for an implantable pressure sensor having wireless communication capability that can account for these artifacts and provide a more accurate reading of the internal pressure to be measured but which uses dynamic calibration systems and methods.

All references cited herein are incorporated herein by reference in their entireties.

BRIEF SUMMARY OF THE INVENTION

A pressure sensor that is implantable within a living being for detecting a pressure (e.g., intracranial pressure (ICP), blood pressure, lung pressure, etc.) present at a location wherein the pressure sensor is implanted is disclosed. The implantable pressure sensor comprises: a sensor housing comprising one side formed by a first flexible membrane; and wherein the sensor housing further comprises sensor electronics including a force transducer in contact with the first flexible membrane for detecting flexing of the first flexible membrane when the flexible membrane is exposed to the pressure present at the location; and wherein the force transducer is positioned on a second flexible membrane, wherein the second flexible membrane permits the force transducer to be moved into contact and out of contact with the first flexible membrane for statically and dynamically calibrating the implantable pressure sensor.

A method for calibrating a pressure sensor in situ within a living being for detecting a pressure (e.g., intracranial pressure (ICP), blood pressure, lung pressure, etc.) present at a location within the living being is disclosed. The method comprises: disposing a pressure sensor within the living being wherein the pressure sensor comprises a force transducer in contact with a first flexible membrane, forming a portion of an outer surface of the pressure sensor, that is exposed to the pressure present at the location; positioning the force transducer on a second flexible membrane such that the force transducer is in contact with the first flexible membrane; displacing the force transducer to a first position to be out of contact with the first flexible membrane and measuring the force required to achieve such a first position to form an initial calibration point; oscillating the force transducer at the first location and collecting a first set of displacement data as the force transducer is oscillated; deriving a first dynamic force calibration point from the first set of displacement data; displacing the force transducer to a second position that is even further out of contact with the first flexible membrane than the first position and measuring the force required to achieve the second position; oscillating the force transducer at the second location and collecting a second set of displacement data as the force transducer is oscillated; deriving a second dynamic force calibration point from the second set of displacement data; and establishing a force calibration characteristic based on the first and second sets of displacement data.

A method for calibrating a pressure sensor in situ within a living being for detecting a pressure (e.g., intracranial pressure (ICP), blood pressure, lung pressure, etc.) present at a location within the living being is disclosed. The method comprises: disposing a pressure sensor within the living being wherein the pressure sensor comprises a force transducer in contact with a first flexible membrane, forming a portion of an outer surface of the pressure sensor, that is exposed to the pressure present at the location; positioning the force transducer on a second flexible membrane that forms an upper surface to an internal housing that is suspended by a third flexible membrane to an inner wall of the pressure sensor and wherein the force transducer is in contact with the first flexible membrane; displacing the force transducer to a first position to be out of contact with the first flexible membrane and measuring the force required to achieve such a first position to form an initial calibration point; oscillating the force transducer at the first location and collecting a first set of displacement data as the force transducer is oscillated; deriving a first dynamic force calibration point from the first set of displacement data; displacing the force transducer to a second position that is even further out of contact with the first flexible membrane than the first position and measuring the force required to achieve the second position; oscillating the force transducer at the second location and collecting a second set of displacement data as the force transducer is oscillated; deriving a second dynamic force calibration point from the second set of displacement data; and establishing a force calibration characteristic based on the first and second sets of displacement data.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The invention of the present application thereof, it will be apparent to one skilled in the art that various changes and modifications can be made therein without departing from the spirit and scope thereof.

Figure 3:
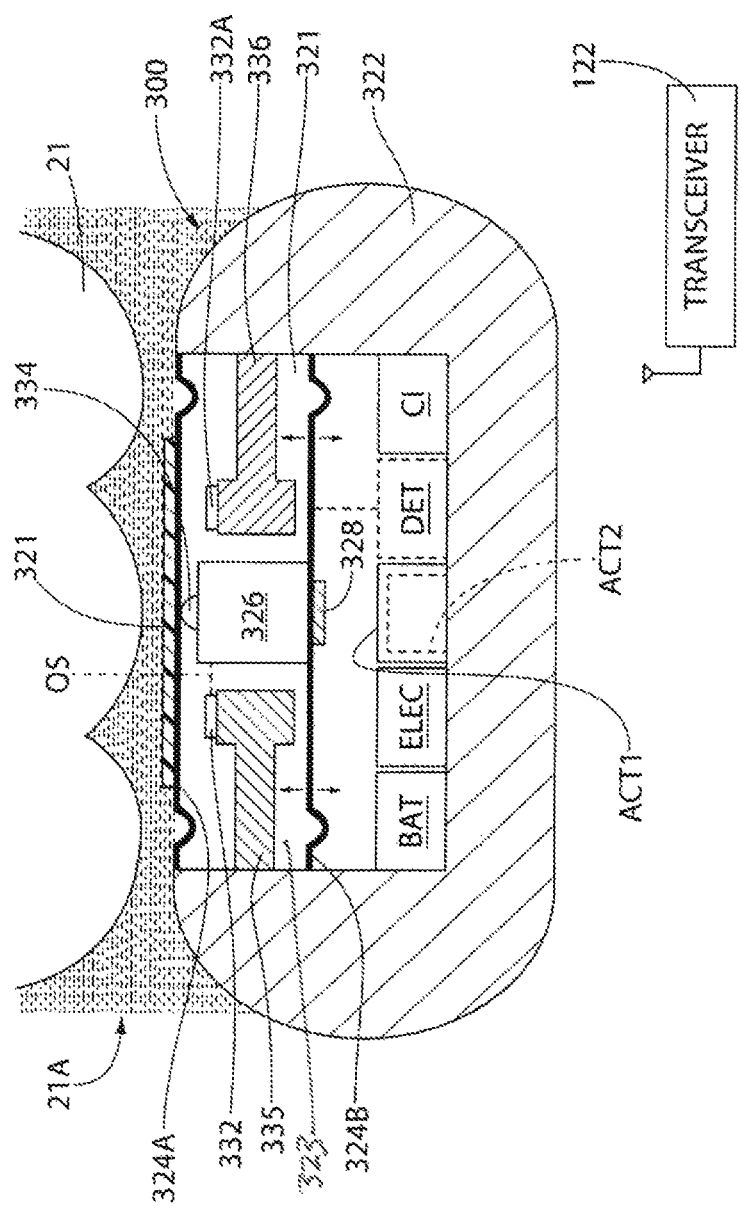
FIG. 3 is an enlarged cross-sectional view of a first embodiment of the implantable sensor of the present invention showing the pressure/force transducer at the reference position.

As shown in FIG. 3, the present invention comprises an implantable pressure sensor 300 and a remotely-located transceiver 122. The sensor 300 is positioned within or adjacent the brain 21, such that the implantable pressure sensor 300 is exposed to the cerebrospinal fluid (CSF) 21A. As a result, internal pressure CSF data obtained from the implantable sensor 300 is then transmitted wirelessly to the remotely-located transceiver 122.

Figure 3A:
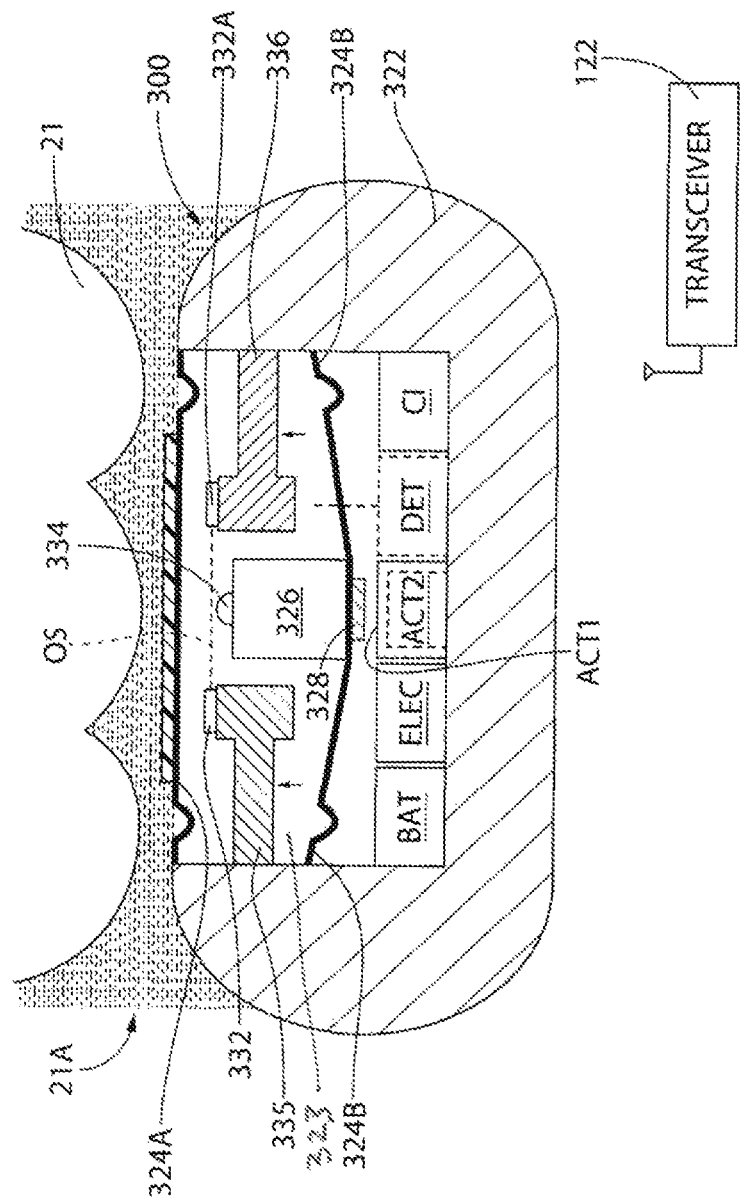
FIG. 3A is similar to FIG. 3 but depicts the pressure/force transducer being displaced away from the upper membrane.

The implantable pressure sensor 300 comprises a rigid housing 322 having a cavity 323 in which the internal components of the implantable pressure sensor 300 are located. The sensor 300 comprises a pair of elastic or flexible membranes 324A and 324B. The upper or outer flexible membrane or "CSF membrane" 324A forms the contact surface with the CSF 21A and experiences the intracranial pressure (ICP); a rigid part of this flexible membrane is shown by element 321 (e.g., a non-metallic layer). The lower or internal flexible membrane 324B supports a pressure/force transducer 326 (e.g., a piezoresistive pressure (e.g., low pressure sensor SM5103 or SM5106 by Silicon Microstructures Inc.)). An actuator ACT (e.g., an electromagnet, microelectromechanical system (MEMS) or other miniature actuator, etc.) is used to drive the pressure/force transducer 326 up or down within the cavity 323 for implantable pressure sensor calibration purposes as well as to assess bio-fouling of the upper membrane 324A, or to even dislodge build-up of bio material against the upper surface of the membrane 324A. By way of example only, and as mentioned earlier, the miniature actuator ACT may comprise an electromagnetic actuator (e.g., micro-speaker L0008A-003 by Jong Gar Xin Tech. Co., Ltd.; micro device Spektrum SPMSA2005; etc.) that drives a paramagnetic, diagmagnetic or magnetic (e.g., ferromagnetic) plate 328. By way of example only, where a magnetic plate is used for the plate 328, the electromagnetic actuator magnetically couples to the magnetic plate 328 that is positioned on the lower side of the inner flexible membrane 324B. Furthermore, the actuator ACT may even comprise two distinct actuators; one actuator ACT1 that provides a strong/slow force (also referred to as "large displacement") on the magnetic plate 328 to displace the transducer 326 to engage or disengage from the upper flexible membrane 324A; and a second actuator ACT2 that provides a weak/fast force (also referred to as "small displacement") that vibrates the transducer 326 at a desired frequency/amplitude, as will discussed later. Subsequent use of the term "actuator ACT" throughout this Specification is meant to encompass both scenarios: either a single miniature actuator that provide both types of forces or a pair of miniature actuators that provide the respective forces. Thus, by way of example only, FIG. 3 depicts the relative positions of the components when the actuator ACT is not energized, hereinafter known as the reference position or "x=0 displacement" position; FIG. 3A depicts the relative positions of the components when the actuator ACT has applied the strong/slow force to move the pressure/force transducer 326 away from the CSF membrane 324A.

It should be understood that the materials used in the implantable sensor 300 (as well as the implantable sensor 400, to be discussed below) comprise bio-compatible materials, especially those sensor components/surfaces that are in direct contact with bio-material. As result, the cross-sectional views shown in the figure do not necessarily indicate metal material and are used simply to indicate a cross-sectional of the component.

The implantable sensor 300 further comprises an internal power source (e.g., a battery BAT) for powering transducer electronics ELEC and a communication interface CI. The battery BAT may be a rechargeable type, receiving a recharge signal from the remotely-located transceiver 122. It should be understood that the battery BAT is by way of example only and that the implantable sensor 300 may be a passive device that receives its electrical energy from the remotely-located transceiver 122 or other well-known external recharge device. The transducer electronics ELEC further comprises a microcontroller 330 (FIG. 9; e.g., MSP430xG461x Mixed Signal Microcontroller by Texas Instruments). The microcontroller 330 controls/communicates with the actuator ACT, the communication interface CI, as well as an optical sensor 332 or alternatively, a detector DET. The optical sensor 332 emits an optical signal OS whose interruption by a known mass 334, positioned on top of the transducer 326, alerts and indicates to the microcontroller 330 the displacement of the transducer 326; a target or reflector 332A is aligned with the emitter of the optical sensor 332 and both the emitter 332 and reflector 332A are fixed at aligned positions on respective support members 335 and 336. Alternatively, a detector DET (e.g., an infrared detector) can also be used to measure the overall displacement of the transducer 326. The media within the cavity 323 may comprise air, an inert gas or a vacuum. A signal conditioner takes the raw data signal from the pressure/force transducer 326 and conditions it (e.g., amplifies, filters, etc.) for use by the microcontroller 330.

Implantable Sensor Calibration

The present invention solves some of the problems usually associated with implantable sensors. It provides with an easy calibration method which lessens stability requirements and enables obtaining the correct measured value (e.g. ICP), even if sensor offset or sensor sensitivity is altered. The key is that the sensor can be calibrated in situ once implanted.

To address this concern, the present invention involves the following calibration technique on the force transducer. In particular, the method involves calibrating the sensor in-place before the measured quantity (e.g., ICP) reading is taken. This calibration technique assures that the parameters that affect the reading are taken into account and therefore their effects are nullified.

In order to calibrate the sensor 300, it is necessary to develop a force calibration characteristic and although there are several ways to achieve this, the preferred method is via a "2-point" calibration method where two verifiable force points are defined to create the linear calibration characteristic. The 2-point calibration is achieved using the commands shown in parts A and B of FIG. 4. The initial force point is achieved by disengaging the transducer 326 from the upper membrane 324A and noting the force used to achieved this disengagement. The second force point is achieved by applying a vibratory force to the transducer and deriving the force from a plurality of displacement data, e.g. $F = m \cdot d^2 x / dt^2$ where F is the force, m is the known mass and x is the displacement.

Figure 4:
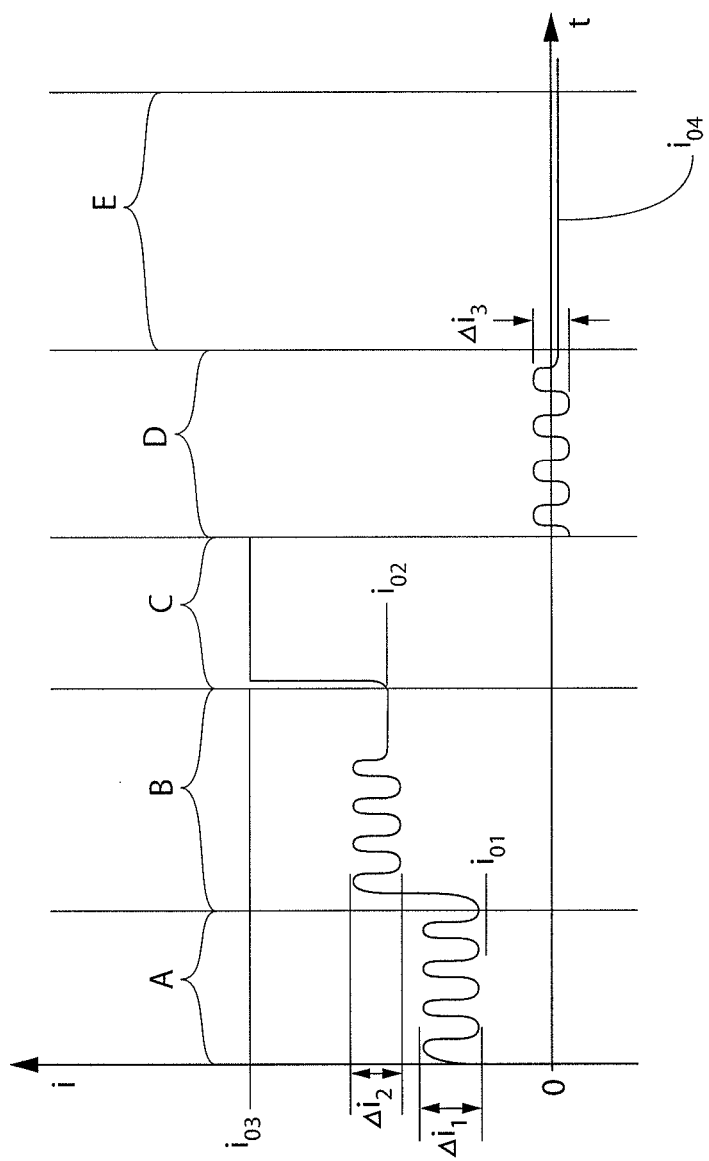
FIG. 4 is a timing diagram depicting the various activation commands to achieve calibration of the implantable sensor of the present invention.

FIG. 4 sets forth a timing diagram depicting the various actuator ACT activation commands to achieve calibration of the implantable sensor 300 and membrane assessment. Sections A-B are used for 2-point calibration, sections C and E are used for static calibration of the internal membrane 324B while section D is used for dynamic calibration of the internal membrane 324B. By way of example only, if the miniature actuator ACT forms a single actuator, under section A, a positive DC current command ($i_{o1}$) is applied to displace the mass 334/transducer 326 away from the upper membrane 324A and then a oscillatory signal ($\Delta i_1$) is applied to vibrate the transducer 326. Under section B, a further positive DC signal is applied ($i_{o2}$) to displace the transducer 326 even further away from the upper membrane 324A, and another oscillatory signal ($\Delta i_2$). In section C, a large positive DC signal ($i_{o3}$) is applied alone to evaluate the stiffness of the internal membrane 324B. In section D, only a vibratory signal ($\Delta i_{o3}$) is applied to the transducer 326 which causes the CSF membrane to oscillate and thereby assess if any bio-matter build-up has occurred on the CSF membrane 324A and to dislodge it via the vibratory motion. In section E, a negative DC command ($i_{o4}$) is applied to cause the pressure/force transducer 326 to move upward causing the CSF membrane 324A to move upward.

It should be understood that displacing the known mass 334 away from the upper membrane 324A before applying the oscillatory signal allows any tension in the upper membrane 324A caused by the engagement of the known mass 334 with the membrane 334A to be removed.

Figure 5:
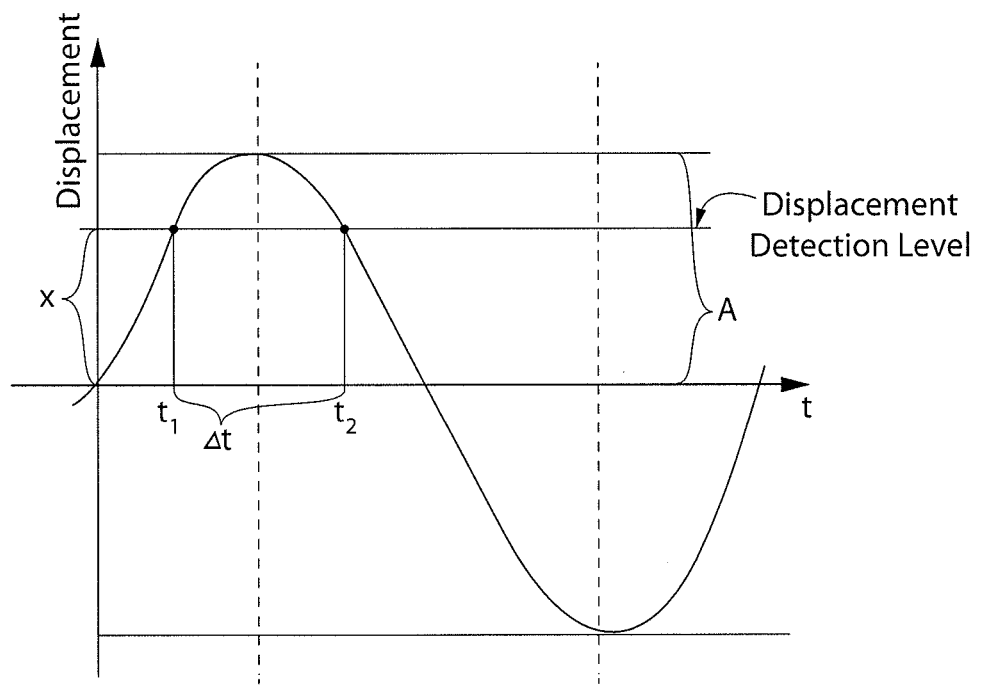
FIG. 5 depicts an exemplary sinusoidal vibration signal used for dynamic calibration.

As shown in FIG. 5, the transducer 326 is vibrated with a known frequency in accordance with the sinusoidal characteristic $A \cdot \sin(\omega)t = x$, where x is the vertical displacement. By taking the second derivative of this quantity, the force can be found. However, the only "knowns" are the frequency ($\omega$), the phase (when the vibratory signal is initiated and terminated) and the displacement at any point, via the optical sensor 332/332A which is positioned at a predetermined "x" value away from a reference point. In order to determine the second force point, it is necessary to determine the amplitude A of the vibratory signal, which as mentioned previously, is unknown. One way to determine the amplitude A is to simply calculate it from a single measurement of $t=t_1$ when the top of the known mass 334 interrupts the optical signal OS; alternatively, and in addition, when the optical signal OS is restored as the top of the known mass 334 displaces downward, when $t=t_2$, the amplitude A can also be calculated. As mentioned previously, a plurality of similar amplitude calculations can be conducted over several cycles of the known frequency and from that data, the force calibration characteristic can be determined.

Figure 6:
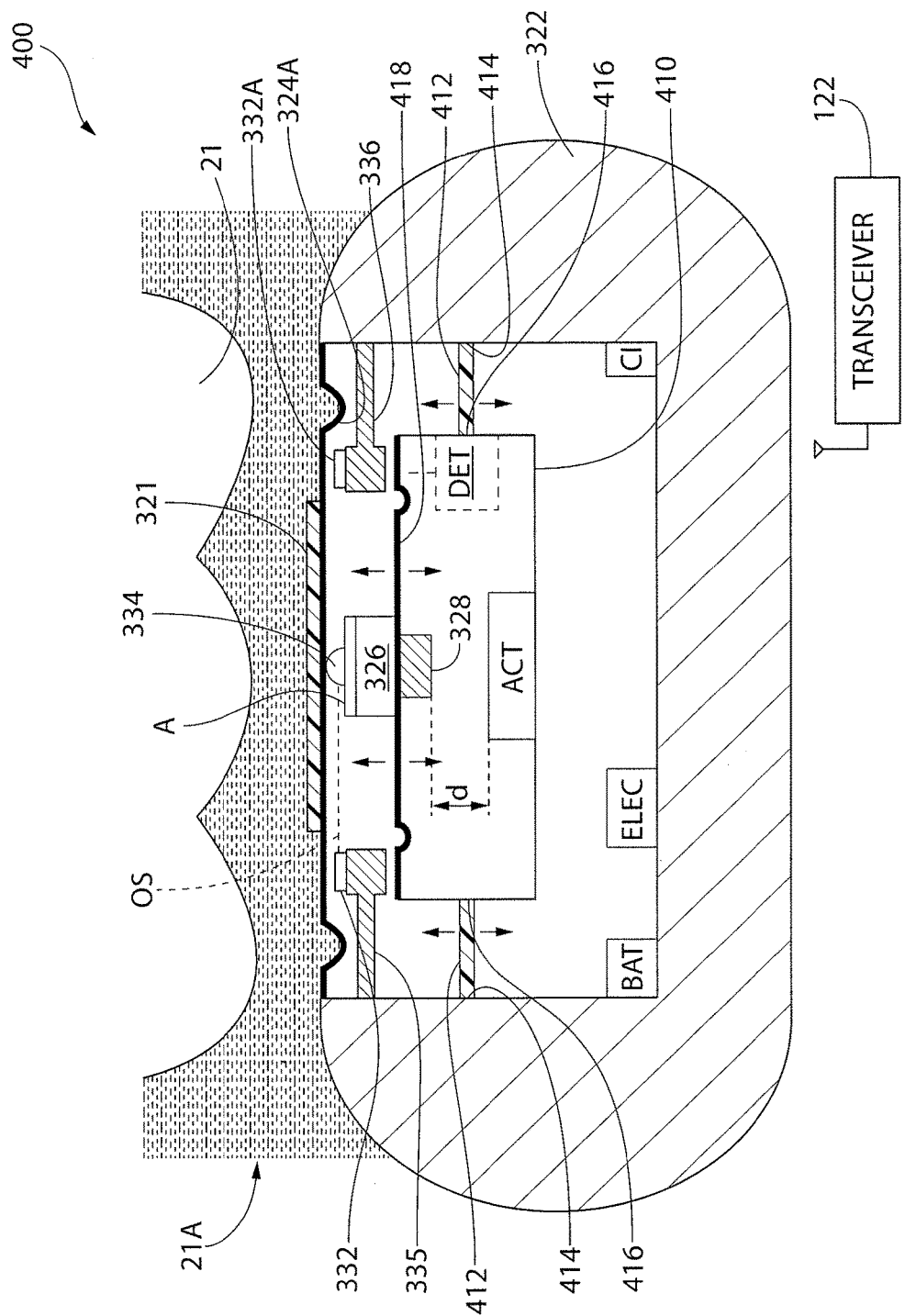
FIG. 6 is a cross-sectional view of a second embodiment of the implantable sensor of the present invention utilizing a "floating vibrator" for achieving dynamic calibration.

FIG. 6 depicts a second embodiment 400 of the implantable pressure sensor, also referred to as a "floating vibrator." In this configuration, the actuator ACT itself is suspended on a third flexible membrane. In particular, the implantable pressure sensor 400 comprises an internal housing 410 that is suspended within the cavity 321 by a third flexible membrane 412. This flexible membrane 412 is secured at its outer side 414 to the sensor housing 322 and to the internal housing 410 on its inner side 416. The upper surface of the internal housing 410 comprises a flexible membrane 418 to which the pressure/force transducer 326 is coupled to the membrane's 418 upper side and to which the magnetic plate 328 (or alternatively a paramagnetic or ferromagnetic grain, etc.) is coupled to the membrane's 418 lower side. As with the first embodiment 300, the pressure/force transducer 326 has a known mass 334 that is in contact with the upper or CSF membrane 324A when the actuator ACT is not energized. The optical sensor 332/332A and the detector DET operate similarly to that described with regard to the first embodiment 300, as well as the electronics ELEC and communication interface CI.

In operation, the actuator ACT generates a non-contact field (e.g., an electromagnetic field) that attracts or repels the magnetic plate 328 (or alternatively a paramagnetic or ferromagnetic grain, etc.) in a cyclical manner, as described earlier with regard to the first embodiment 300, using both DC or vibratory commands as also described earlier. The fluctuations in intensity of the magnetic field are sinusoidal. However, unlike the first embodiment 300, because the actuator ACT is also suspended on the flexible membrane 412, when the actuator ACT pulls or repels the pressure/force transducer 326, the actuator ACT also displaces, thereby maintaining a constant separation distance "d" between the pressure/force transducer 326 and the actuator ACT. Acceleration caused by the up/down movement of the vibrator's membrane 418 generates calibrating forces acting on the sensing area SA of the pressure/force transducer 326 (due to the attached known mass 334). The membrane 412 on which the vibrator internal housing 410 is mounted can freely move due to initial forces, but can also be moved by additional actuators (not shown) in order to shift it upwards or downwards.

As mentioned previously, the sensors 300 or 400 include a communication interface (CI) for wirelessly transmitting collected pressure data to the transceiver 122. As will be discussed in detail later, the communication format may include radio communication, infrared communication, etc., and the present invention is not limited to any particular communication methodology.

Figure 7:
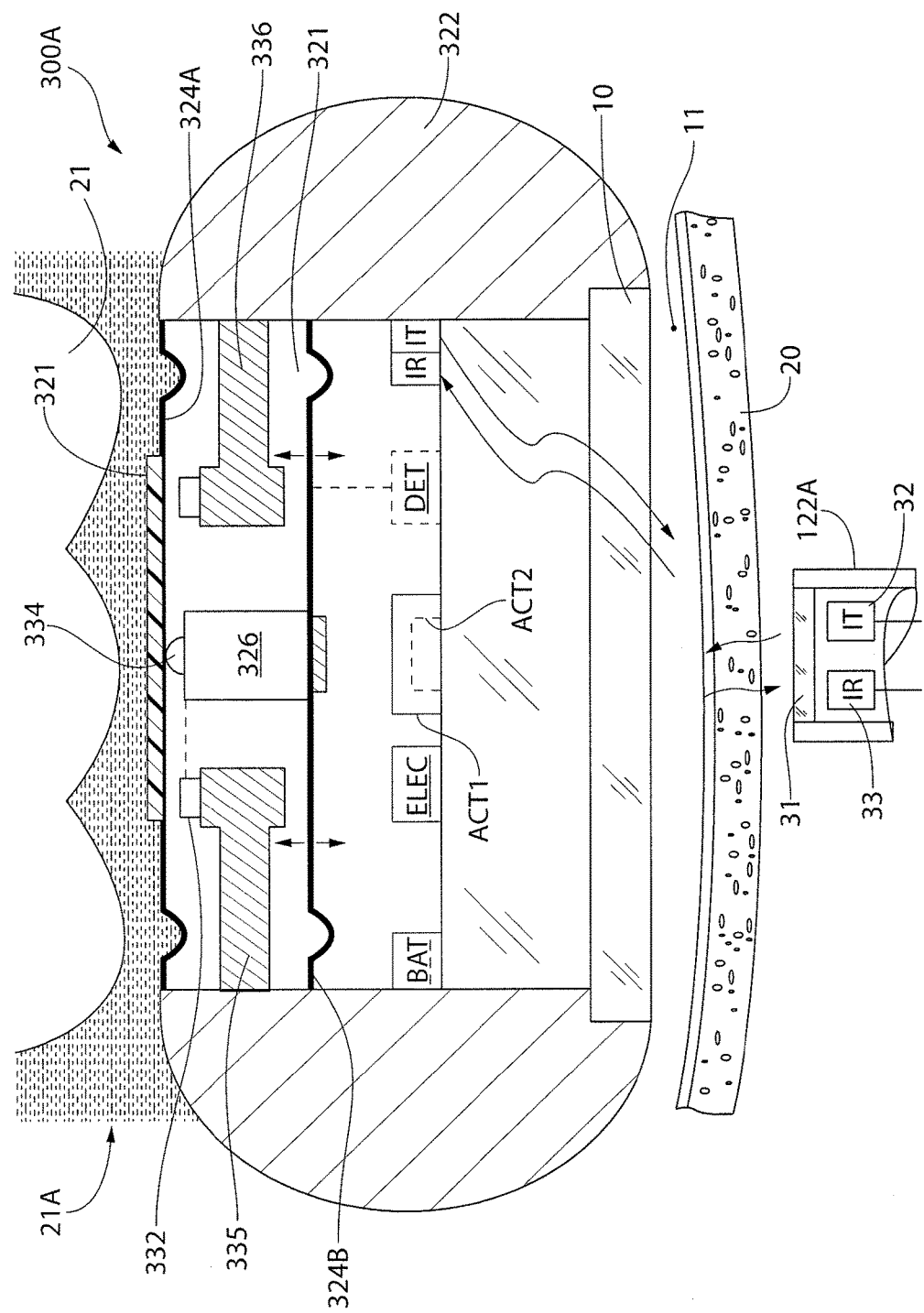
FIG. 7 is an enlarged cross-sectional view of the first embodiment of the implantable sensor of the present invention including a transparent window for infrared communication.
Figure 8:
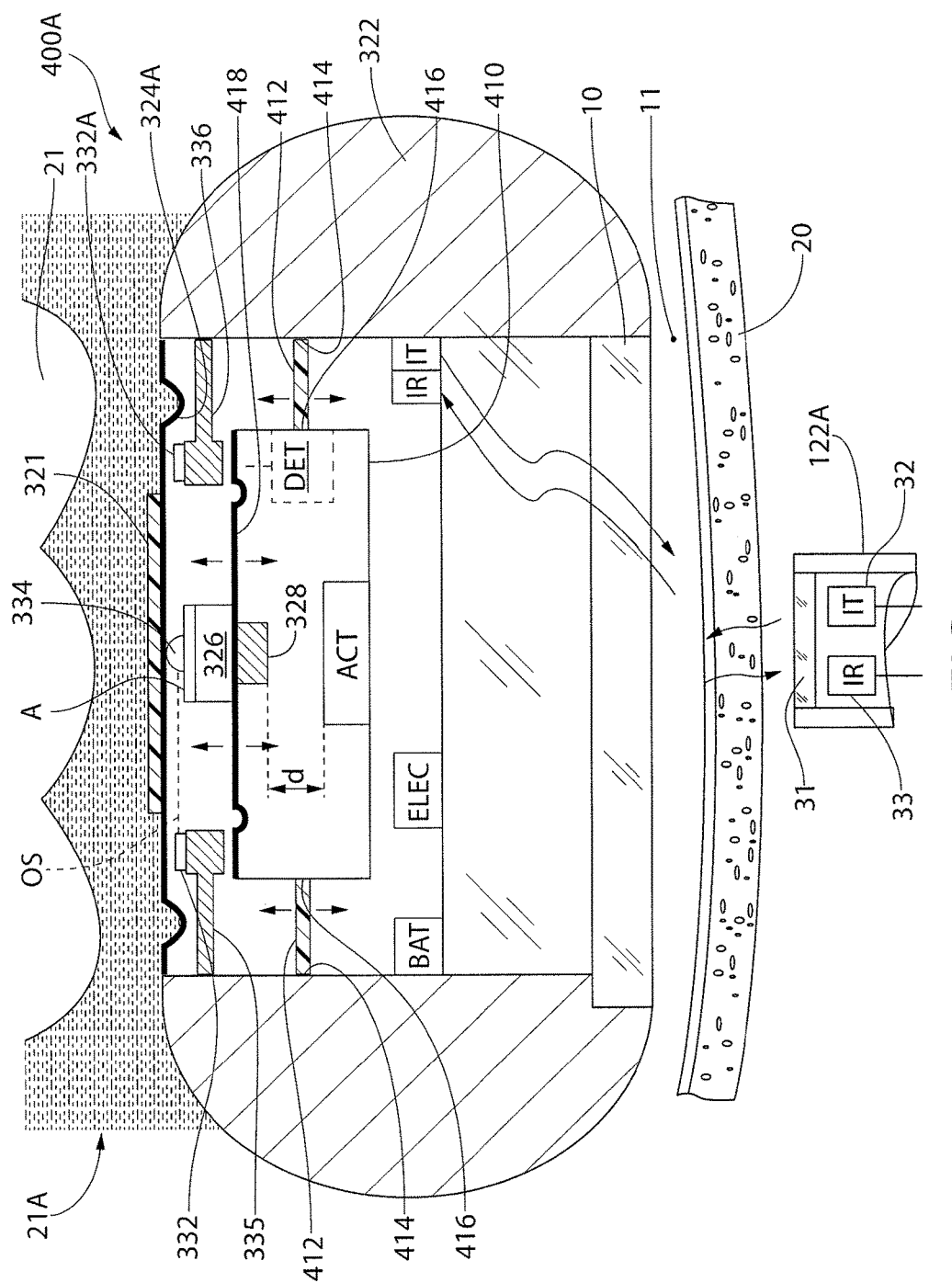
FIG. 8 is an enlarged cross-sectional view of the second embodiment of the implantable sensor of the present invention including a transparent window for infrared communication.

FIGS. 7-8 discloses a particular example of a communication interface CI in that the communication mechanism is an infrared communication mechanism. In particular, the implantable sensor 300 or 400 includes a communication mechanism having an LED transmitter 8 (e.g., emitter OP200 by TT Electronics) and an LED receiver 9 (phototransistor OP500 by TT Electronics). Thus, measured internal pressure values can be detected by the sensor 300 or 400 and then transmitted out of the living being to a remotely-located infrared transceiver 122A. Similarly, the LED receiver 9 can be used to receive electromagnetic energy (e.g., infrared light) to charge the battery BAT or, if the implantable sensor is a passive device, to drive the electronics ELEC.

Figure 1A:
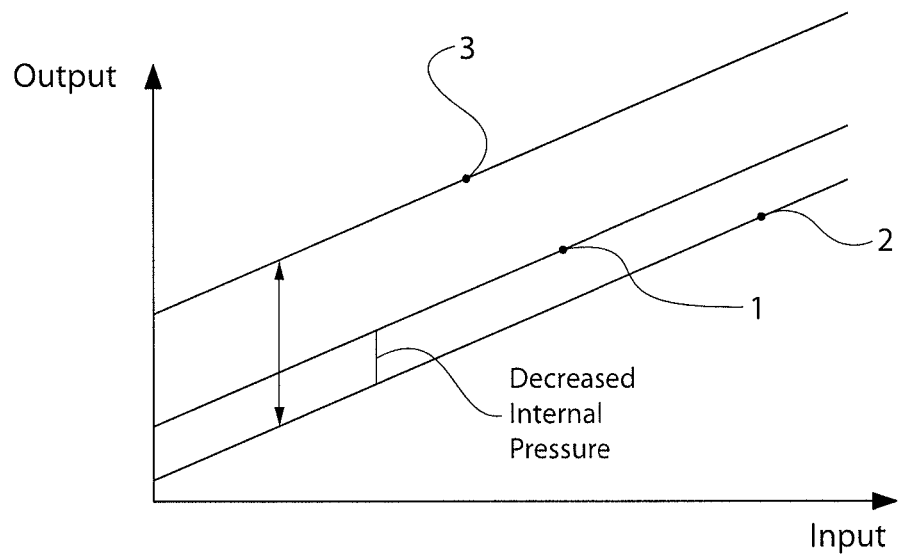
FIG. 1A is a prior art graph that depicts how the input-output relationship changes with internal (i.e., inside the sensor body) pressure.
Figure 1B:
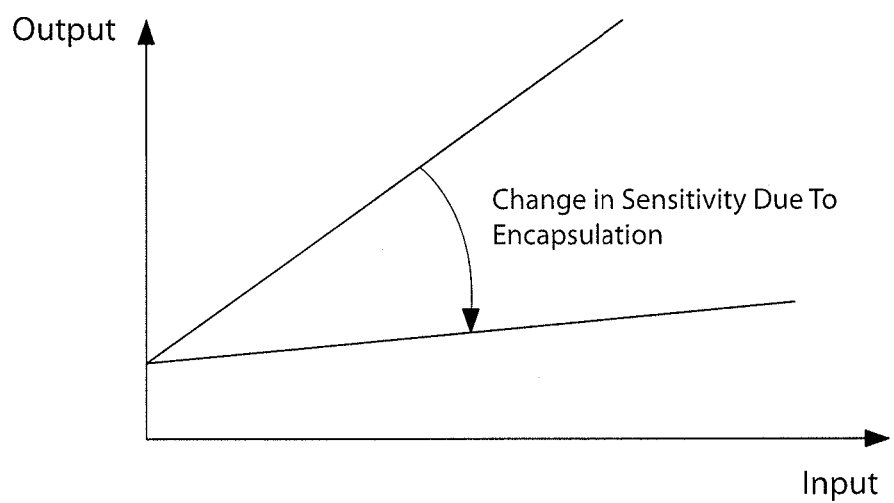
FIG. 1B is a prior art graph that shows how the input-output relationship changes due to protein buildup on the surface of the sensor.
Figure 2:
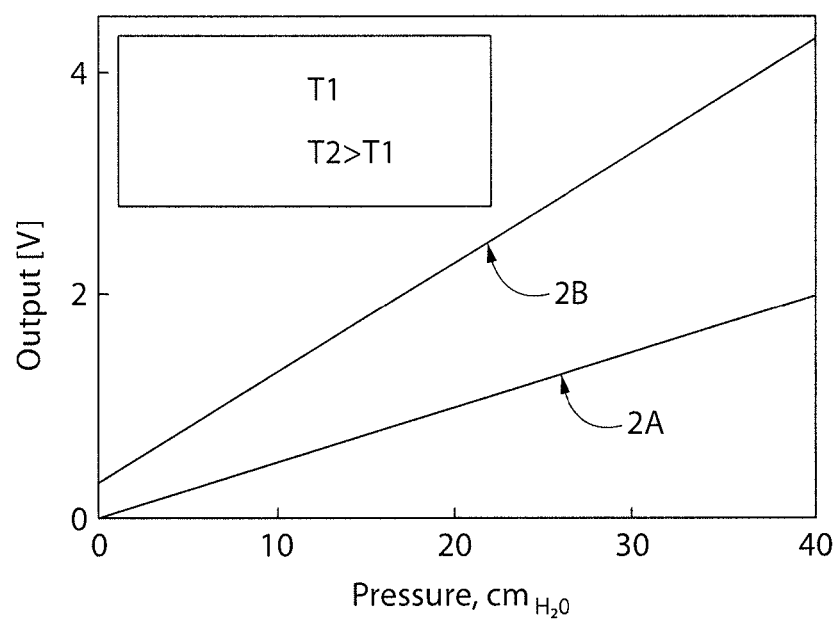
FIG. 2 is a prior art graph showing how changes in temperature affect sensor sensitivity.

To effect the infrared communication, the side of the sensor housing 332 directly opposite the transmitter 8/receiver 9 pair comprises a transparent material (e.g., plexiglass) 10 that permits the passage of the infrared energy between the implantable sensor 300/400 and the infrared receiver 122A. By way of example only, when the implantable sensor 300/400 is to measure intracranial pressure (ICP), the sensor 300/400 is implanted within the subarachnoid space 11 of the test subject, as shown in FIG. 2, outside the brain 21, the infrared energy passes through the scalp, skull, dura and arachnoid matter (the combination indicated by the reference number 20). The infrared receiver 122A also comprises an infrared transmitter 32/receiver 33 pair for communicating with the implantable sensor 300/400 and also includes a transparent distal end 31 for allowing passage of the infrared energy.

Figure 9:
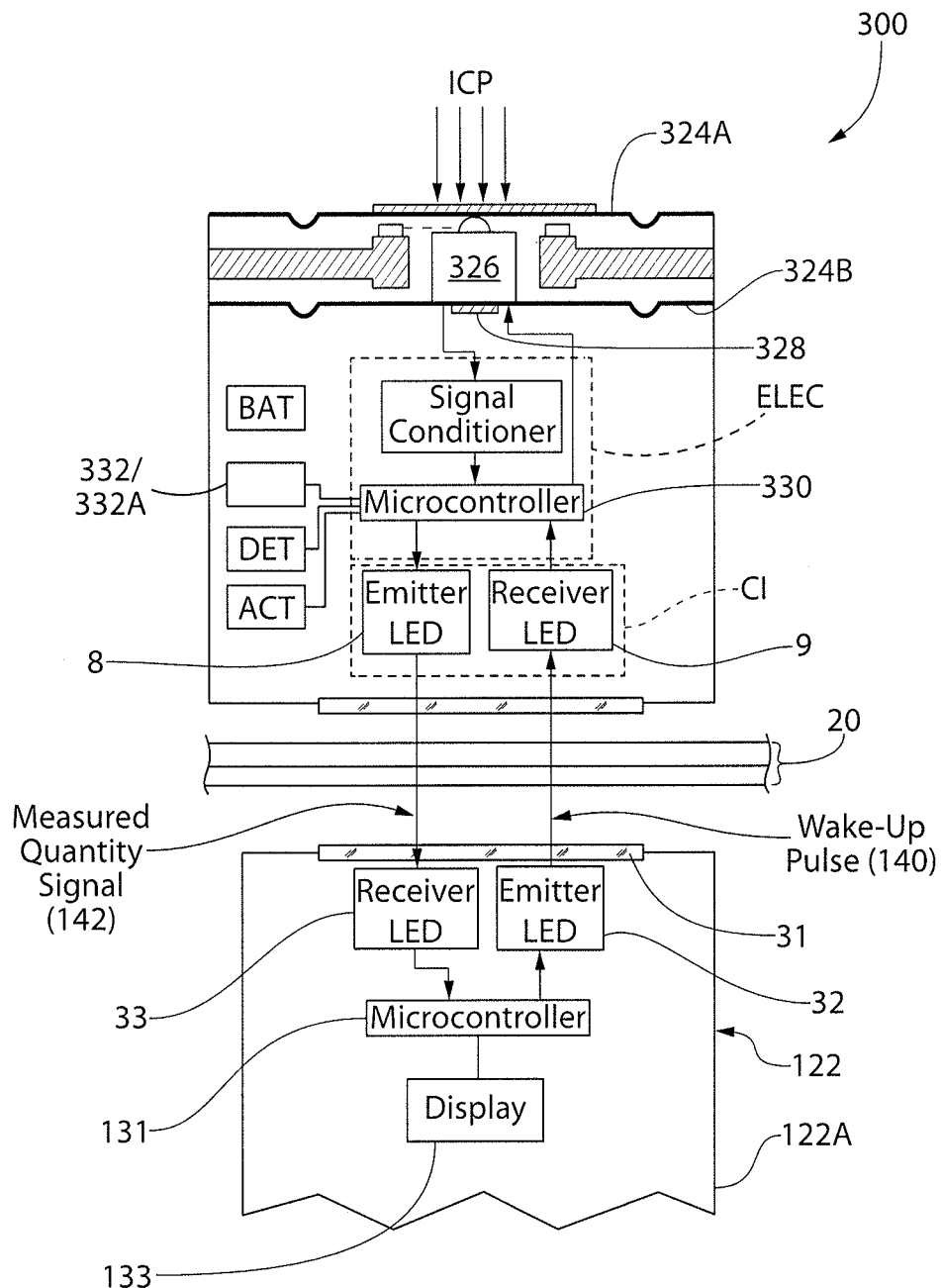
FIG. 9 is a block diagram showing the non-contact communication of the implantable sensor with a remotely-located transceiver.

FIG. 9 provides a block diagram of the CI of the sensors 300/400 and the corresponding communication interface of the transceiver 122. The transducer's 326 electrical signal corresponding to the pressure is conditioned (e.g., amplified and filtered) by a signal conditioner and is digitized by the microcontroller 330 before being wirelessly transmitted (e.g., an ICP signal) to the transceiver 122A via the emitter LED 8. An LED receiver 33 then passes this to a microcontroller 131 for processing and ultimate display 133 or other output to the operator or user. An emitter LED 32 provides input/commands to the implantable pressure sensor 120A.

It should be noted, as mentioned earlier, that the microcontroller 330 controls the operation of the sensor 300/400, including the transducer electronics ELEC, the actuator ACT, and the emitter LED 8.

As mentioned earlier, implantable pressure sensor 300/400 is powered from the internal battery BAT or from the receiver 122/122A utilizing electromagnetic waves (RF or IR) transmitted through the skin, tissue and/or bone. The measured quantity, e.g., pressure, is detected using an active sensor principle where the energy from the measured quantity is conditioned by the signal conditioner. In the preferred embodiment, information about the measured signal is converted to a frequency coded message and, for example, optically (e.g., infrared) transmitted outside the body to the receiver (see FIGS. 3-3A, 6-14). When the transceiver 122A is activated by the user, the transceiver 122A sends an infrared pulse to the sensor 300/400. This signal wakes up (also referred to as a "start command") the microcontroller 330 which controls the entire process in order to minimize power consumption. In particular, the steps to measure the signal by the sensor 300/400 are:
1) The microcontroller 330 turns on the pressure/force transducer 326 (e.g., piezoresistive die) and its signal conditioner;
2) Digitizing of the measured quantity (e.g., ICP) value;
3) Frequency modulating the measured (e.g., ICP) value;
4) Transmitting the frequency via infrared energy;
5) Implantable sensor goes to sleep.

One problem that this configuration encounters is the occasional occurrence of the output signal (i.e., the measured quantity signal 142) triggering the microcontroller 330 when the working wavelength of the "wake-up" signal 140 (e.g., transmitted infrared signal) and the measured quantity signal 142 (e.g., ICP signal) are the same. This problem is solved by two different methods. A first solution uses software whereby the microcontroller 330 overrides the wake up interruption signal 140 until the measured quantity signal 142 is sent; however this reduces the availability of ports in the microcontroller 330. A second solution is the use of two different wavelengths for signals 140 and 142 that do not interfere with one another. The latter solution is the preferred method since it takes advantage of some microcontroller inherent hardware benefits that prevents false triggering of the implantable sensor 300/400.

Figure 10:
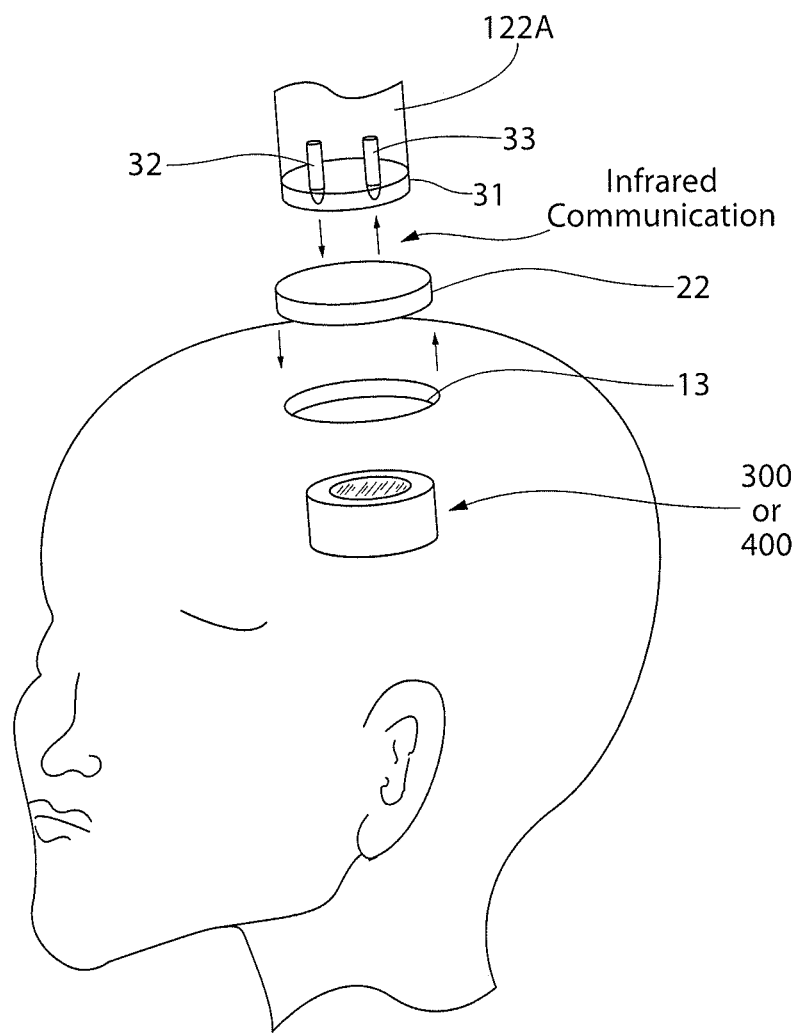
FIG. 10 depicts how the implantable sensor is positioned within the living being, e.g., within the head of a human, and how the implantable sensor communicates with an external hand-held portion.
Figure 11:
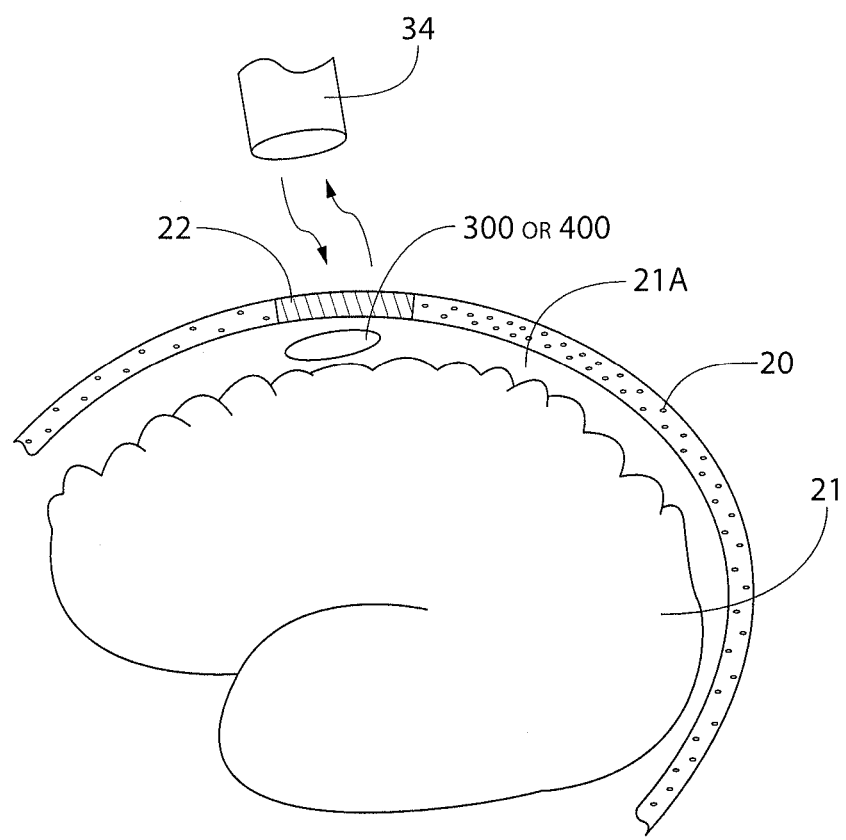
FIG. 11 is a partial view of the head of a living being wherein the implantable sensor is placed within the subarachnoid space and which allows for infrared or radio communication with the handheld device.

FIG. 10 depicts how the implantable sensor 300/400 is positioned when used to measure ICP. In particular, a piece 22 of the skull is removed during trepanation to form a burr hole 13 and permit implantation of the sensor 300/400 in the brain, as discussed earlier with respect to FIG. 3-9. The sensor 300/400 is positioned with its transparent surface 10 facing outward to transmit/receive infrared energy outwardly of the skull towards the remotely-located transceiver 122A. Once the sensor 120A is positioned, the piece 22 of skull is re-inserted within the burr hole 13 and sensor 120A-transceiver 122A communication occurs as shown in FIG. 10. Therefore, although the implantable sensor 300/400 and the transceiver 122A require the use of respective transparent surfaces 10 and 31, infrared transmission through the scalp/skull/dura, arachnoid matter 20 does occur without major disruption of the infrared signals, as shown in FIG. 11.

Figure 12:
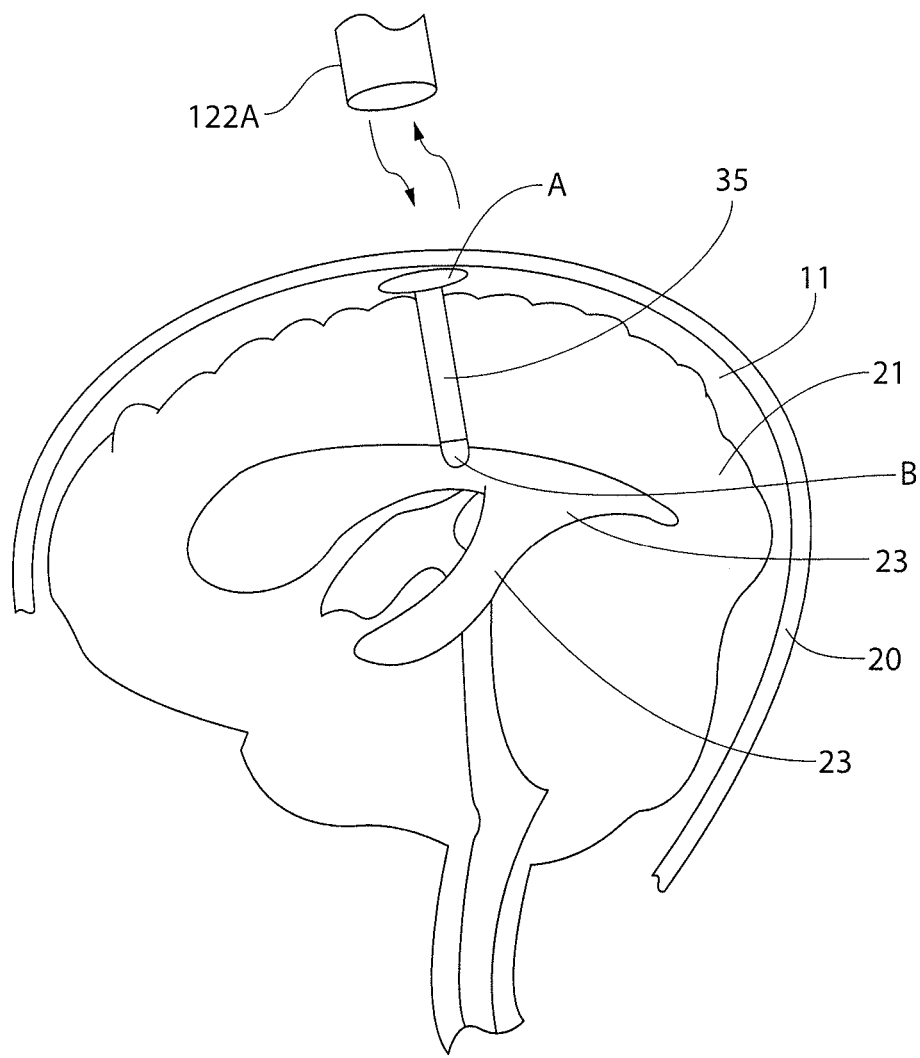
FIG. 12 depicts another preferred embodiment of the implantable sensor wherein the transducer-membrane assembly portion of the implantable sensor is placed at a distal end of a catheter and the transceiver portion of the sensor is positioned at a proximal end of the catheter for communicating with the hand-held device.
Figure 13:
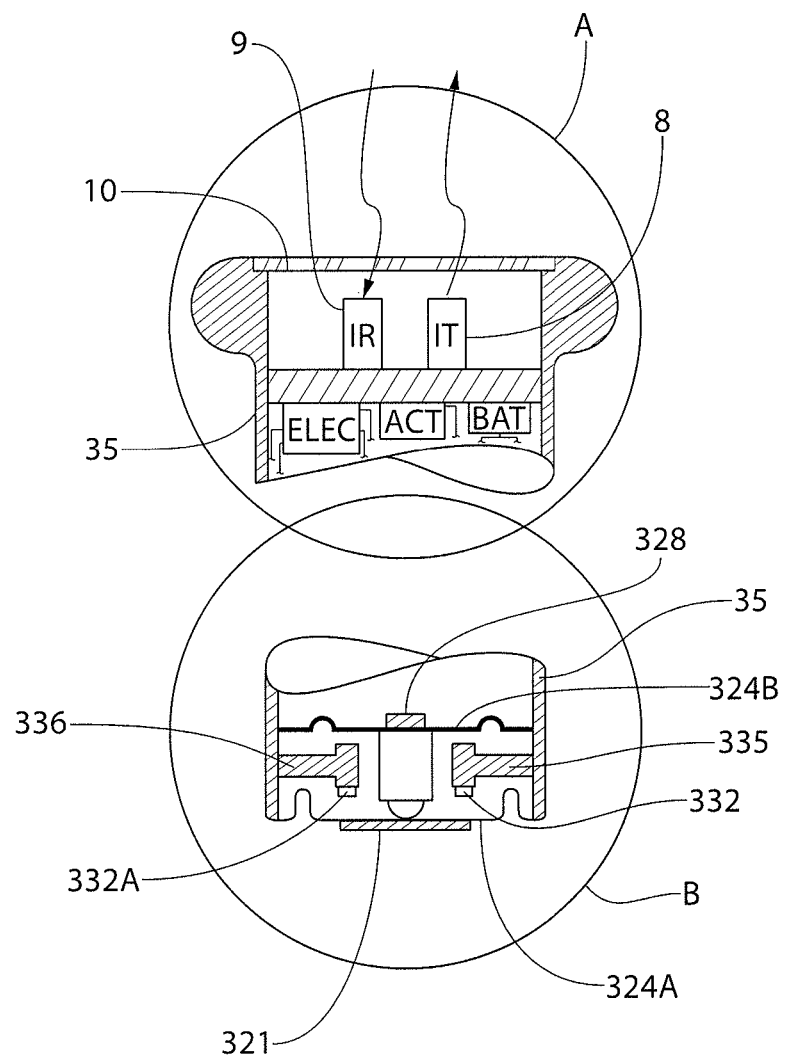
FIG. 13 is an enlarged view of the proximal end (A) and of the distal end (B) of the embodiment of FIG. 12.
Figure 14:
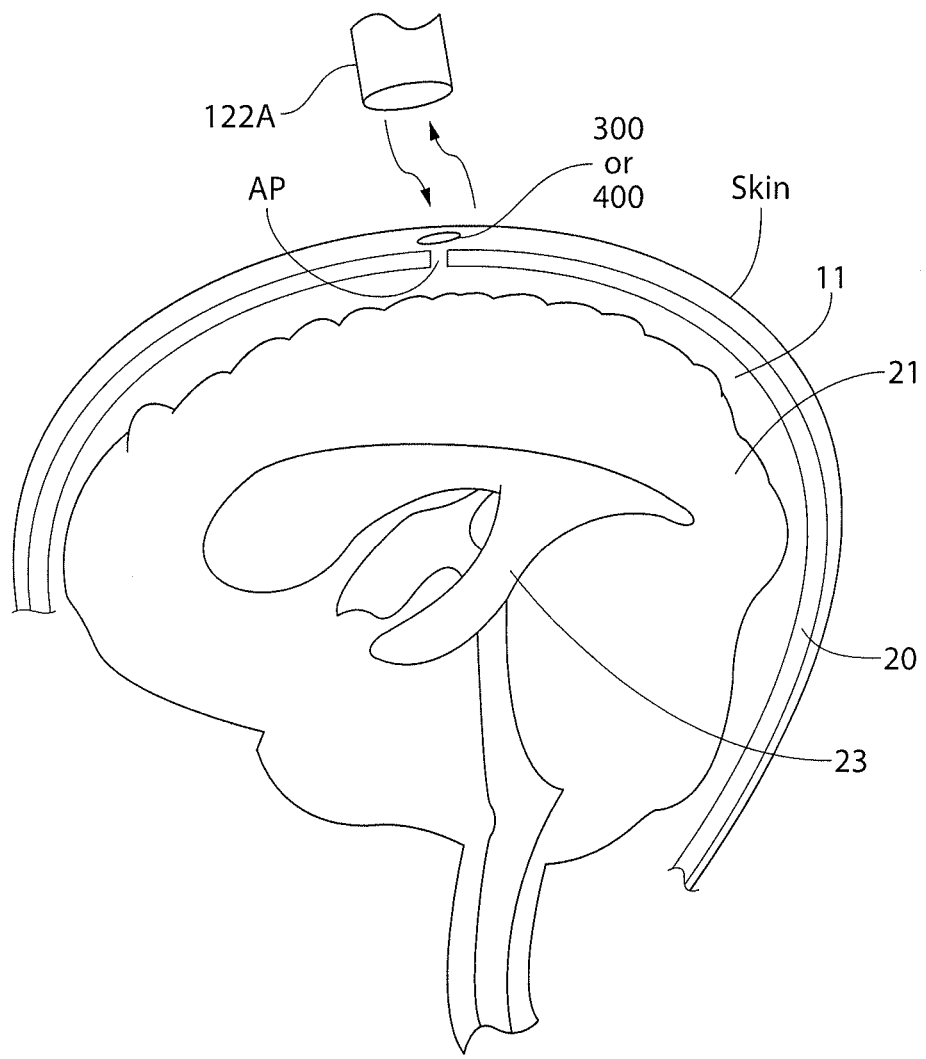
FIG. 14 depicts an alternative position of the implantable pressure sensor being disposed just underneath the skin and against the skull.

A further embodiment 120B, as shown in FIGS. 12-13, distributes the implantable sensor at the proximal and distal ends of a catheter 35. In particular, as shown most clearly in FIG. 12, the communication portion A of the sensor 300/400 is positioned at the proximal end of the catheter 35 which is located within the subarachnoid space 11; the pressure sensing portion B is located at the distal end of the catheter 35 within the brain ventricle 23 (FIG. 12). This configuration permits the pressure sensing portion B to be located within smaller and more critical areas of the brain without having to introduce the entire implantable pressure sensor 300/400 within such critical areas. It should be understood that the brain ventricle and subarachnoid space are shown by way of example only and that other implantation locations are within the broadest scope of the invention. The key feature is that the communication portion A is located more closely to the outside of the living being to facilitate the wireless communication with the remotely-located transceiver 122/122A while permitting the pressure sensing to occur within a deeper location within the living being. An alternative example is shown in FIG. 14: the implantable sensor 300/400 may be positioned above the skull 20 but under the skin. A small aperture AP is made in the skull to expose the implantable sensor 300/400 to the CSF and thus the ICP.

While the invention has been described in detail and with reference to specific examples thereof, it will be apparent to one skilled in the art that various changes and modifications can be made therein without departing from the spirit and scope thereof.

What is claimed is:
1. A pressure sensor comprising:
a sensor housing comprising one side formed by a first flexible membrane, wherein said first flexible membrane is configured to flex when exposed to a pressure present in fluid of a living being;
said sensor housing further comprising sensor electronics including a force transducer movable into contact with and out of contact with said first flexible membrane;
at least one actuator for moving said force transducer into contact with and out of contact with said first flexible membrane; and
at least one microcontroller controlling said at least one actuator.

2. The pressure sensor of claim 1, wherein said at least one actuator is capable of causing said force transducer to experience oscillatory motion.

3. The pressure sensor of claim 1, wherein said at least one actuator is selected from the group consisting of an electromagnetic actuator and a microelectromechanical actuator.

4. The pressure sensor of claim 1, wherein said first flexible membrane is mounted to a rigid sensor housing and said first flexible membrane comprises a rigid portion separated from the sensor housing by a flexible portion.

5. The pressure sensor of claim 1, wherein the force transducer is mounted on a second flexible membrane spaced a distance from said first flexible membrane.

6. The pressure sensor of claim 1, further comprising a radio frequency transmitter for transmitting a pressure measured at said first flexible membrane to a remotely-located receiver.

7. The pressure sensor of claim 1, further comprising an infrared transmitter for transmitting a pressure measured at said first flexible membrane to a remotely-located receiver.

8. The pressure sensor of claim 1, further comprising an infrared receiver for receiving a start command from a remotely-located transmitter.

9. The pressure sensor of claim 8, further comprising a rechargeable battery and wherein said rechargeable battery obtains its recharging energy via said infrared receiver.

10. The pressure sensor of claim 1, wherein said pressure sensor is implantable in the head of the living being.

11. The pressure sensor of claim 10, additionally comprising a catheter having a proximal end and a distal end, said distal end comprising said force transducer and said first flexible membrane disposed at a first location within said head of said living being.

* * * * *